(12) United States Patent  
Kleyman

(10) Patent No.: US 9,078,696 B2
(45) Date of Patent: Jul. 14, 2015

(54) SURGICAL RETRACTOR INCLUDING POLYGONAL ROLLING STRUCTURE

(75) Inventor: Gennady Kleyman, Brooklyn, NY (US)

(73) Assignee: Covidien LP, Mansfield, MA (US)

(\*) Notice: Subject to any disclaimer, the term of this patent is extended or adjusted under 35 U.S.C. 154(b) by 590 days.

(21) Appl. No.: 13/439,997

(22) Filed: Apr. 5, 2012

(65) Prior Publication Data

US 2012/0283520 A1 Nov. 8, 2012

Related U.S. Application Data

(60) Provisional application No. 61/481,380, filed on May 2, 2011.

(51) Int. Cl.
*A61B 1/32* (2006.01)
*A61B 17/34* (2006.01)

(52) U.S. Cl.
CPC ..... *A61B 17/3431* (2013.01); *A61B 2017/3429* (2013.01); *A61B 2017/3435* (2013.01); *A61B 2017/3443* (2013.01)

(58) Field of Classification Search
CPC ........... A61B 17/0293; A61B 17/3431; A61B 17/3423; A61B 17/02; A61B 2017/3427; A61B 2017/3435
USPC .................................. 606/201–246
See application file for complete search history.

(56) References Cited

U.S. PATENT DOCUMENTS

| 5,159,921 | A | 11/1992 | Hoover |
| 5,366,478 | A | 11/1994 | Brinkerhoff et al. |
| 5,524,644 | A | 6/1996 | Crook |
| 5,582,577 | A | \* 12/1996 | Lund et al. ..................... 600/204 |
| 5,810,721 | A | \* 9/1998 | Mueller et al. ................. 600/206 |
| 5,906,577 | A | 5/1999 | Beane et al. |
| 6,033,428 | A | 3/2000 | Sardella |
| 6,077,288 | A | 6/2000 | Shimomura et al. |
| 6,382,211 | B1 | 5/2002 | Crook |
| 6,450,983 | B1\* | 9/2002 | Rambo ........................... 602/60 |
| 6,589,167 | B1 | 7/2003 | Shimomura et al. |
| 6,723,044 | B2 | 4/2004 | Pulford et al. |
| 6,846,287 | B2 | 1/2005 | Bonadio et al. |

(Continued)

FOREIGN PATENT DOCUMENTS

| EP | 1312318 | 12/2005 |
| EP | 2181657 | 5/2010 |

(Continued)

OTHER PUBLICATIONS

European Search Report dated May 7, 2012 for EP 11 19 3738.
U.S. Appl. No. 13/091,246, filed Apr. 21, 2011 Paul D. Richard.
U.S. Appl. No. 13/030,164, filed Feb. 18, 2011, Gennady Kleyman.
U.S. Appl. No. 13/030,172, filed Feb. 18, 2011, Gennady Kleyman.
U.S. Appl. No. 13/030,178, filed Feb. 18, 2011, Gennady Kleyman.

(Continued)

*Primary Examiner* — Mary Hoffman

(57) ABSTRACT

A surgical access port is provided for insertion through an incision in a patient and generally includes a flexible sleeve having a roller assembly provided at a proximal end of the flexible sleeve and a flexible ring affixed to a distal end of the flexible sleeve. The roller assembly includes a plurality of rollers mounted on a polygonal frame assembly and engageable with the proximal end of the flexible sleeve. The polygonal frame assembly includes a plurality of shafts, interconnected by corner members, and rotatably supporting the plurality of rollers. The rollers include longitudinally extending flutes interspersed with longitudinally extending ribs connected to the proximal end of the flexible sleeve.

15 Claims, 8 Drawing Sheets

(56) References Cited

U.S. PATENT DOCUMENTS

| | | |
|---|---|---|
| 6,958,037 B2 | 10/2005 | Ewers et al. |
| 7,033,319 B2 | 4/2006 | Pulford et al. |
| 7,081,089 B2 | 7/2006 | Bonadio et al. |
| 7,238,154 B2 | 7/2007 | Ewers et al. |
| 7,377,898 B2 | 5/2008 | Ewers et al. |
| 7,393,322 B2 | 7/2008 | Wenchell |
| 7,445,597 B2 | 11/2008 | Butler et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,650,887 B2 | 1/2010 | Nguyen et al. |
| 7,704,207 B2 | 4/2010 | Albrecht et al. |
| 7,727,146 B2 | 6/2010 | Albrecht et al. |
| 7,951,076 B2 | 5/2011 | Hart et al. |
| 7,998,068 B2 | 8/2011 | Bonadio et al. |
| 2003/0139767 A1 | 7/2003 | Jespersen |
| 2003/0176771 A1* | 9/2003 | Pulford et al. ............. 600/208 |
| 2003/0187376 A1 | 10/2003 | Rambo |
| 2003/0192553 A1* | 10/2003 | Rambo .................... 128/850 |
| 2004/0049099 A1* | 3/2004 | Ewers et al. ............. 600/206 |
| 2004/0260153 A1 | 12/2004 | Pulford et al. |
| 2005/0020884 A1 | 1/2005 | Hart et al. |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2006/0149306 A1 | 7/2006 | Hart et al. |
| 2006/0161050 A1 | 7/2006 | Butler et al. |
| 2006/0247498 A1 | 11/2006 | Bonadio et al. |
| 2007/0088204 A1* | 4/2007 | Albrecht et al. ............ 600/208 |
| 2007/0093695 A1 | 4/2007 | Bonadio et al. |
| 2007/0203398 A1 | 8/2007 | Bonadio et al. |
| 2008/0021360 A1 | 1/2008 | Fihe et al. |
| 2008/0021362 A1* | 1/2008 | Fihe et al. .................. 602/75 |
| 2008/0200767 A1 | 8/2008 | Ewers et al. |
| 2008/0281161 A1 | 11/2008 | Albrecht |
| 2009/0187079 A1 | 7/2009 | Albrecht et al. |
| 2010/0130824 A1 | 5/2010 | Piskun |
| 2010/0191064 A1* | 7/2010 | Nguyen et al. ............. 600/203 |
| 2010/0261973 A1 | 10/2010 | Mollenauer et al. |
| 2010/0312066 A1 | 12/2010 | Cropper et al. |
| 2011/0054260 A1* | 3/2011 | Albrecht et al. ............ 600/208 |
| 2012/0157786 A1* | 6/2012 | Pribanic ..................... 600/208 |
| 2012/0245427 A1* | 9/2012 | Kleyman .................... 600/208 |

FOREIGN PATENT DOCUMENTS

| | | |
|---|---|---|
| WO | WO01/08581 | 2/2001 |
| WO | 01/91652 A1 | 12/2001 |
| WO | WO 03/103548 A1 | 12/2003 |
| WO | WO2004/075741 | 9/2004 |

OTHER PUBLICATIONS

U.S. Appl. No. 13/031,346, filed Feb. 21, 2011, Gennady Kleyman.
U.S. Appl. No. 13/031,352, filed Feb. 21, 2011, Gennady Kleyman.
U.S. Appl. No. 13/193,647, filed Jul. 29, 2011, Russell Pribanic.
U.S. Appl. No. 13/217,717, filed Aug. 25, 2011, Joshua Stopek.
U.S. Appl. No. 13/221,062, filed Aug. 30, 2011, Gregory Okoniewski.
U.S. Appl. No. 13/223,029, filed Sep. 1, 2011, Michael Davis.
U.S. Appl. No. 13/223,330, filed Sep. 1, 2011, Gregory Okoniewski.
U.S. Appl. No. 13/223,336, filed Sep. 1, 2011, Michael Davis.
U.S. Appl. No. 13/223,613, filed Sep. 1, 2011, Greg Fischvogt.
U.S. Appl. No. 13/223,627, filed Sep. 1, 2011, Gregory Okonicwski.
U.S. Appl. No. 13/223,645, filed Sep. 1, 2011, Gennady Kleyman.
U.S. Appl. No. 13/223,659, filed Sep. 2, 2011, Francesco Alfieri.
U.S. Appl. No. 13/223,678, filed Sep. 1, 2011, Gregory Okoniewski.
U.S. Appl. No. 13/223,700, filed Sep. 1, 2011, Gennady Kleyman.
U.S. Appl. No. 13/224,353, filed Sep. 2, 2011, Gennady Kleyman.
U.S. Appl. No. 13/224,354, filed Sep. 2, 2011, Greg Okoniewski.
U.S. Appl. No. 13/224,355, filed Sep. 2, 2011, Anibal Rodrigues Jr.
U.S. Appl. No. 13/224,358, filed Sep. 2, 2011, Andrew Barnes.
U.S. Appl. No. 13/228,937, filed Sep. 9, 2011, Dino Kasvikis.
U.S. Appl. No. 13/228,960, filed Sep. 9, 2011, Russell Pribanic.
European Search Report EP08253236 dated Feb. 10, 2009.
European Search Report EP09251613 dated Mar. 24, 2011.
European Search Report EP10250526 dated Jun. 23, 2010.
European Search Report EP10250638 dated Jul. 19, 2010.
European Search Report EP10250643 dated Jun. 23, 2010.
European Search Report EP10250881 dated Aug. 18, 2010.
European Search Report EP10250885 dated Aug. 18, 2010.
European Search Report EP10250944 dated Jul. 29, 2010.
European Search Report EP10251218 dated Jun. 15, 2011.
European Search Report EP10251317 dated Oct. 15, 2011.
European Search Report EP10251359 dated Nov. 8, 2010.
European Search Report EP10251399 dated Sep. 13, 2010.
European Search Report EP10251486 dated Oct. 19, 2010.
European Search Report EP10251693 dated Feb. 3, 2011.
European Search Report EP10251718 dated Jan. 28, 2011.
European Search Report EP10251751 dated Apr. 28, 2011.
European Search Report EP10251796 dated Jan. 31, 2011.
European Search Report EP10251955 dated Feb. 21, 2011.
European Search Report EP10251983 dated Feb. 15, 2011.
European Search Report EP10251984 dated Feb. 10, 2011.
European Search Report EP10251985 dated Feb. 15, 2011.
European Search Report EP10251986 dated Mar. 7, 2011.
Extended European Search Report dated Jul. 9, 2012 from counterpart Eureopan Application No. 12158885.9.
European Search Report (7 pages) for corresponding EP12166292—mailing date Jul. 25, 2012.

* cited by examiner

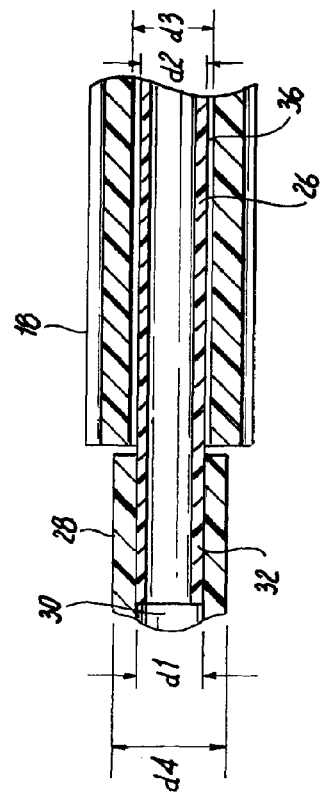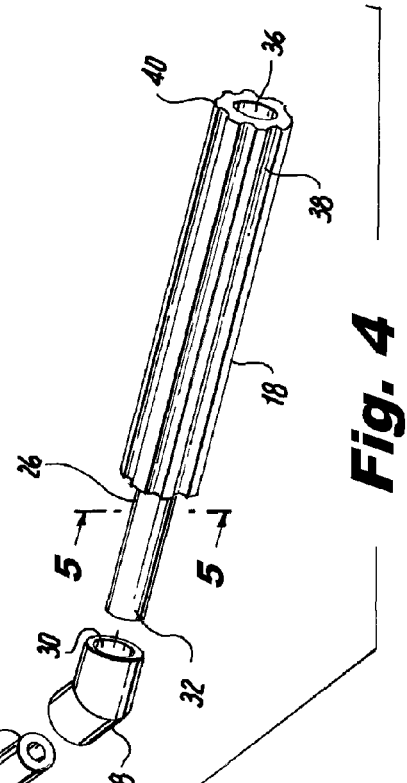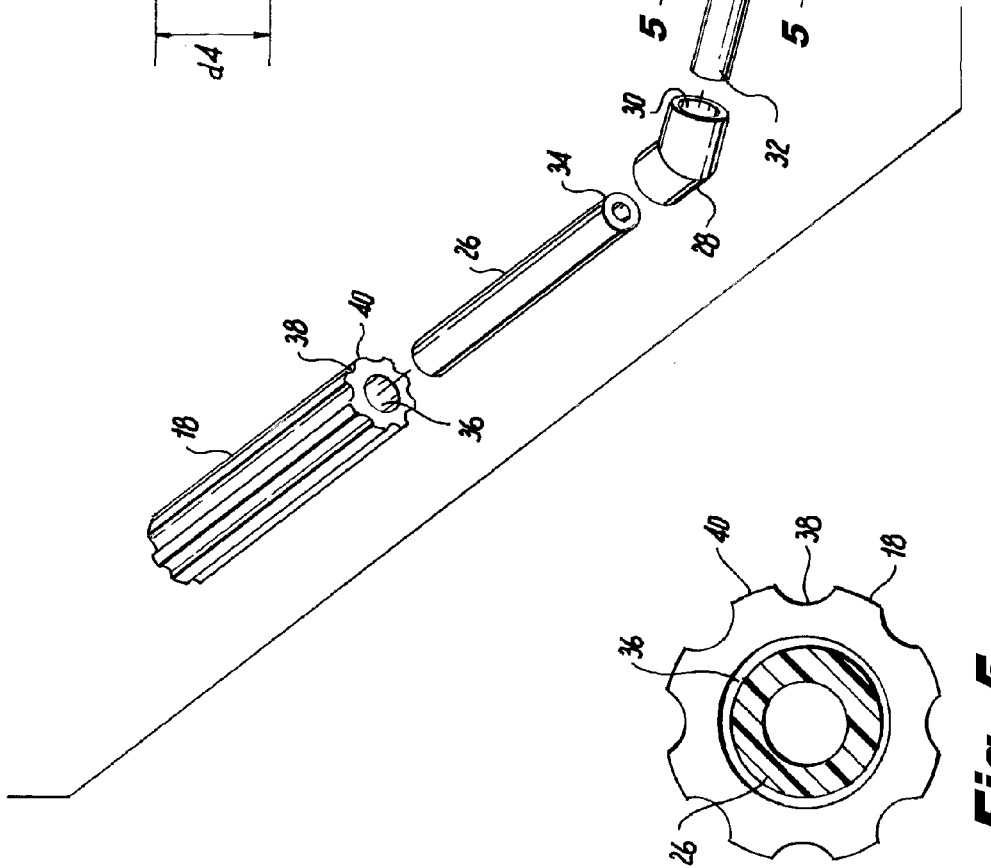

SURGICAL RETRACTOR INCLUDING POLYGONAL ROLLING STRUCTURE

CROSS REFERENCE TO RELATED APPLICATION

The present application claims the benefit of and priority to U.S. Provisional Application Ser. No. 61/481,380, filed on May 2, 2011, the entire contents of which are incorporated herein by reference.

BACKGROUND

1. Technical Field

The present disclosure relates to a surgical retractor including polygonal rolling structure for a surgical access port configured for insertion through an incision formed in the body of a patient. More particularly, the present disclosure relates to a surgical access port having a flexible sleeve and polygonal rolling structure engageable with the flexible sleeve to rotate a proximal end of the flexible sleeve against an outer surface of the patient's body.

2. Background of Related Art

Various surgical procedures are performed in a minimally invasive manner. This includes forming a small incision through a body wall of the patient and inserting an access port through the incision to protect the wound created by the incision and provide a pathway for the insertion of surgical instruments. However, minimally invasive surgery, such as laparoscopy, has several limitations. In particular, surgery of this type requires a great deal of skill in manipulating the long narrow endoscopic instruments to a remote site under endoscopic visualization. To this end, hand-assisted laparoscopic techniques and procedures have been developed. These procedures include both laparoscopic and conventional surgical methodologies. The hand assisted technique is performed in conjunction with a hand access port which is an enlarged device positionable in, for example, the insufflated abdominal cavity, through the incision.

When choosing an access port, care must be taken to ensure that the access port has sufficient length to completely pass through the body wall of the patient. Additionally, the access port must be chosen such that it does not extend too far into the body cavity and obstruct the surgical procedure. Often times it is necessary to access a large area of the body cavity with a minimal number of access ports. In this situation, the surgeon is often limited by the angle at which the surgeon can insert surgical instruments through the access port. Further, care must be taken to prevent movement of the access port during the surgical procedure.

Therefore, it is desirable to provide a surgical access port which is adjustable to provide a low-profile relative to the outer surface of the patients body in order to achieve a greater range of access for the surgeon's hand and/or the surgical instruments inserted through the surgical access port. Additionally, it is further desirable to provide a surgical access port which can be secured or locked into position about the tissue penetrated regardless of the thickness of the tissue encountered.

SUMMARY

There is disclosed a surgical access port including a flexible sleeve having proximal and distal ends and a roller assembly engageable with the proximal end of the sleeve. The roller assembly includes a frame assembly having a multisided shape and a plurality of rollers rotatably mounted on the frame assembly. The frame assembly has a polygonal shape and, in a more particular embodiment, the frame assembly has an octagonal shape. The frame assembly generally includes a plurality of shafts rotatably supporting the rollers. The plurality of shafts is interconnected by corner members.

In one embodiment, the frame assembly, including the plurality of shafts and corner members, is formed as an integral member.

In an alternative embodiment, the frame assembly is formed from a plurality of components including individual shafts and corner members.

In order to prevent binding of the rollers on the corner members, the corner members have an outer diameter greater than an inner diameter of through bores of the rollers. The shafts are formed of a material having a low coefficient of friction to facilitate rotation of the rollers on the shafts.

In a specific embodiment, the rollers include longitudinally extending ribs separated by longitudinally extending flutes and at least one of the longitudinally extending ribs of the rollers are secured to the proximal end of the sleeve to facilitate rolling of the sleeve toward tissue.

In an alternative embodiment, the longitudinally extending ribs are textured so as to facilitate engagement with the proximal end of the sleeve.

The surgical access port further includes a flexible ring, provided on the distal end of the sleeve, to facilitate securing the distal end of the sleeve to an inner surface of tissue.

There is also disclosed a surgical access port including a flexible sleeve having proximal and distal ends and a roller assembly provided at the proximal end of the sleeve. The roller assembly includes a polygonal frame assembly having a plurality of shafts interconnected by corner members and a plurality of rollers rotatably mounted on the shafts. The rollers are engageable with the proximal end of the sleeve. The surgical access port additionally includes a flexible ring affixed to the distal end of the sleeve. In this embodiment, the polygonal frame assembly forms an octagon having eight shafts and eight rollers. The eight rollers are affixed to the proximal end of the sleeve to facilitate rolling the sleeve toward an outer surface of tissue.

There is also disclosed a method of providing a surgical access port in the body of a patient. The method includes providing a surgical access port including a flexible sleeve having proximal and distal ends and a roller assembly engageable with the proximal end of the sleeve. The roller assembly includes a frame assembly having a multisided shape and a plurality of rollers rotatably mounted on the frame assembly and engageable with the proximal end of the flexible sleeve. A flexible ring is provided on the distal end of the flexible sleeve The method includes inserting the distal end of the sleeve through an incision formed in a body wall of a patient by compressing the flexible ring and inserting the flexible ring distally through the incision until it passes into a body cavity. The surgical access port is then tensioned in a proximal direction to bring the flexible ring into engagement with an inner surface of the body wall. The rollers are engaged with the proximal end of the flexible sleeve and rotated to roll the flexible sleeve about the frame assembly and form a rolled portion of the flexible sleeve. The rolled portion of the flexible sleeve is rolled until it engages an outer surface of the body wall.

In a specific method, the rollers are engaged with the proximal end of the flexible sleeve by affixing the rollers to the proximal end of the flexible sleeve.

DESCRIPTION OF THE DRAWINGS

An embodiment of the presently disclosed surgical retractor with polygonal rolling structure for a surgical access port is disclosed herein with reference to the drawings, wherein:

FIG. 4 is a partial perspective view, with parts separated, of a roller assembly of the surgical access port;

FIG. 5 is an end view taken along line 5-5 of FIG. 4;

FIG. 6 is a side view, shown in section, illustrating relative diameters of a roller, a support shaft and a corner member of the roller assembly of the surgical access port;

DETAILED DESCRIPTION OF EMBODIMENTS

An embodiment of the presently disclosed surgical retractor with polygonal rolling structure will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
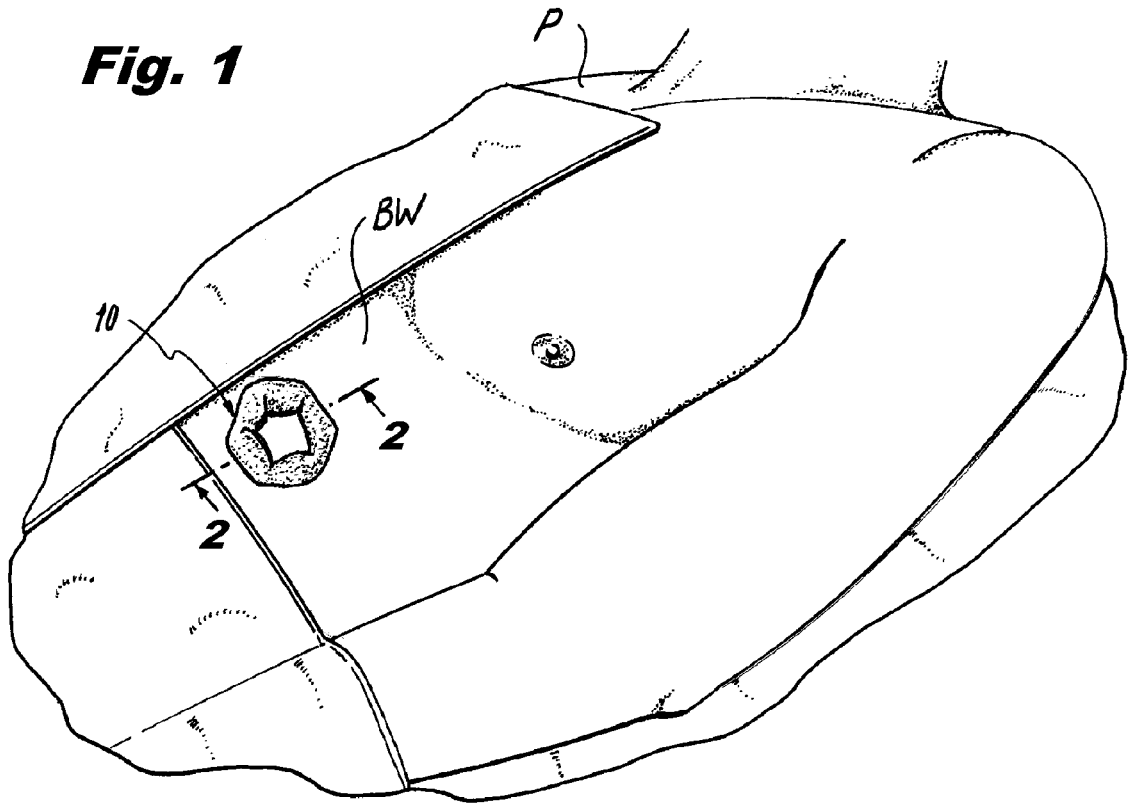
FIG. 1 is a perspective view of the surgical access port positioned through a body wall of a patient.

Referring initially to FIG. 1, there is disclosed a surgical retractor with polygonal rolling structure for a surgical access port 10 inserted through an incision in a body wall BW of a patient P to access, for example, an abdominal cavity. Surgical access port 10 is adjustable to accommodate varying thickness of body tissue and provides a low profile access port to facilitate insertion of the surgeon's hand and/or surgical instruments into a body cavity.

Figure 2:
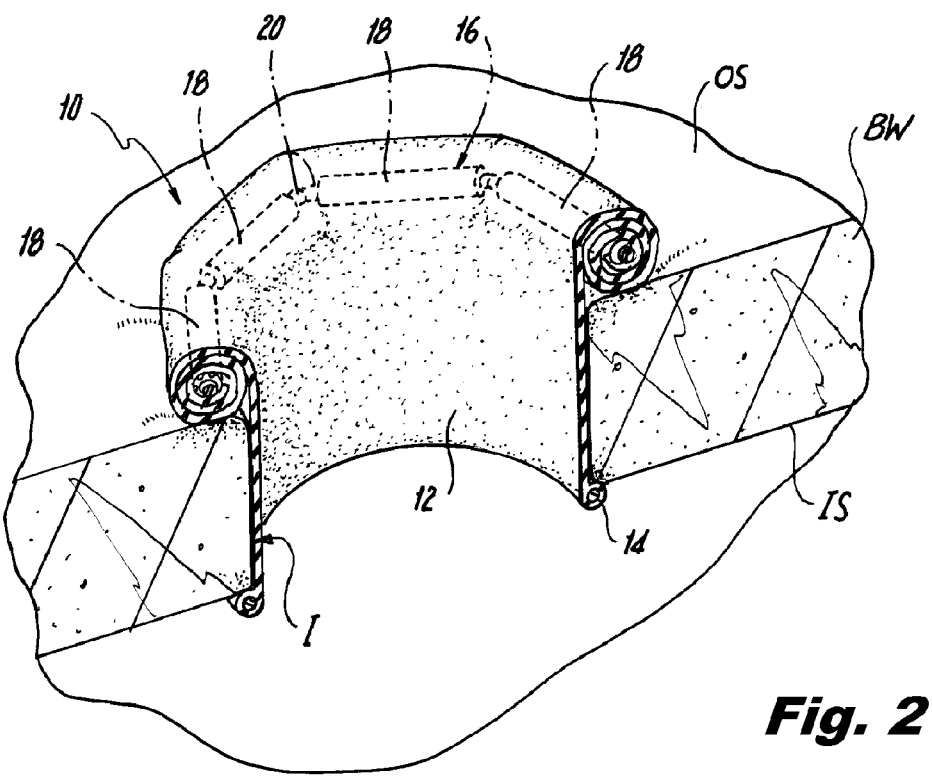
FIG. 2 is a perspective view, shown in section, taken along line 2-2 of FIG. 1.

Referring to FIG. 2, surgical access port generally includes a sleeve 12, an expansion or distal ring 14 and a roller assembly 16. Sleeve 12 is provided to be inserted through an incision I in body wall BW of patient P. Distal ring 14 secures surgical access port 10 against an inner surface IS of body wall BW and roller assembly 16 secures surgical access port 10 against an outer surface OS of body wall BW. Roller assembly 16 generally includes a plurality of rollers 18 rotatably mounted on a top ring or frame assembly 20.

It is contemplated that access port 10 may further include a sealing cap that can be coupled to a proximal end portion of access port 10 to enclose the opening at the proximal end portion of access port 10. The sealing cap may include a seal that defines a slit. The slit is substantially closed in the absence of an object therein, enabling for example, insufflation of the body cavity and providing a substantially fluid-tight barrier across the seal. However, the slit is configured to enable passage of an object, such as the surgeon's hand or a surgical instrument therethrough. The seal may be made from a compressible and/or flexible type material, such as suitable foam or gel material having sufficient compliance to form a seal about the object.

It is further contemplated that a seal anchor member as shown and described in a commonly owned U.S. application Ser. No. 12/244,024, entitled "SEAL ANCHOR FOR USE IN SURGICAL PROCEDURES," which is incorporated by reference herein in its entirety, may be disposed within access port 10. For example, such a seal anchor member may be maintained within an incision by the radially-inwardly directed force exerted by the walls of the incision, with the sleeve being sandwiched between the side of the seal anchor member and the walls of the incision. The seal anchor member permits insufflation of the body cavity and otherwise facilitates a laparoscopic procedure using one or more minimally invasive instruments through the seal anchor member. The seal anchor member may be removed or inserted at any time during the procedure to allow conversion between laparoscopic surgery and open surgery.

Figure 3:
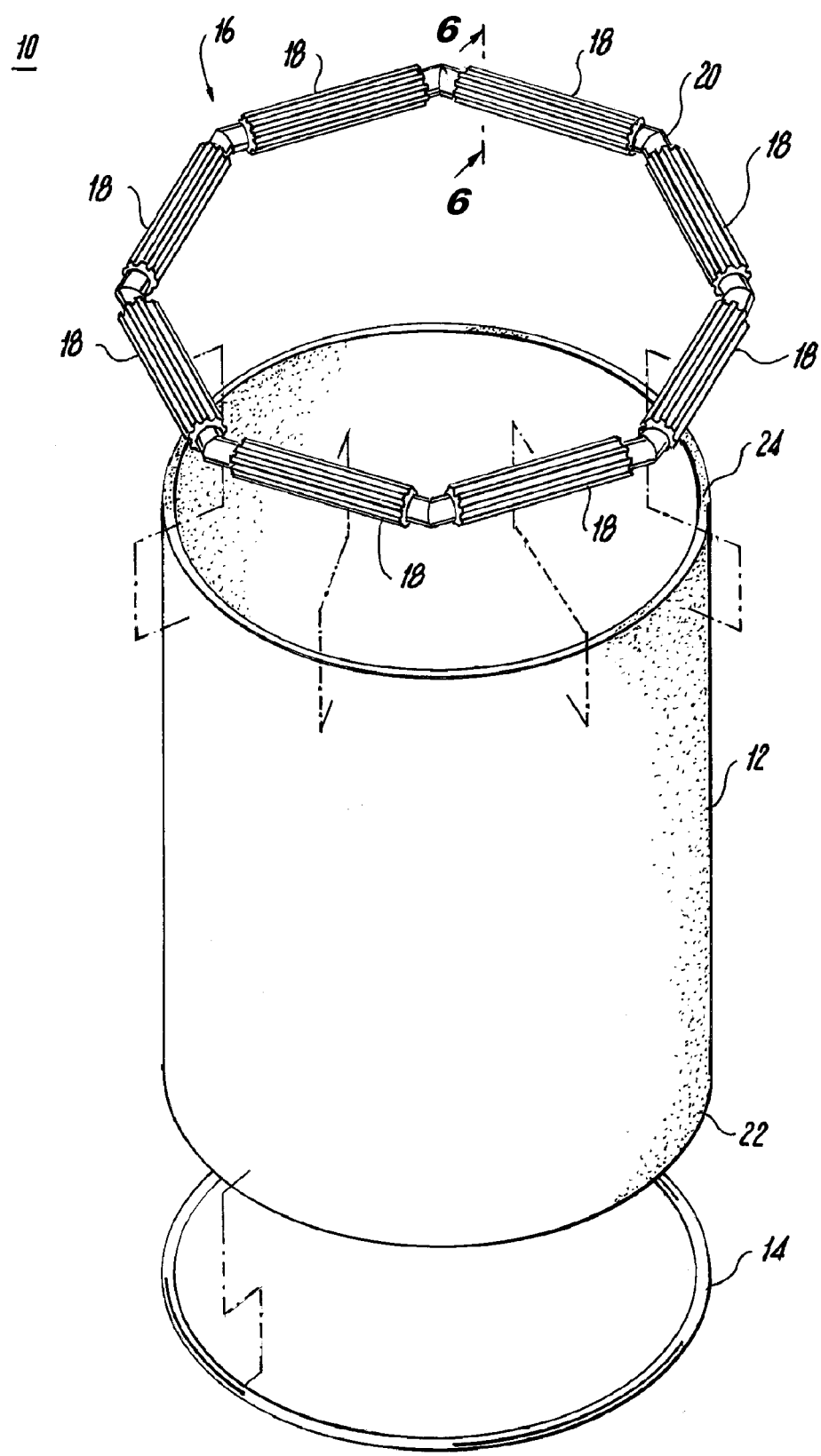
FIG. 3 is a perspective view, with parts separated, of the surgical access port.

Referring now to FIG. 3, distal ring 14 is provided at a distal end 22 of sleeve 12 and is formed from a relatively flexible material. Distal ring 14 may take the shape of a continuous ring or may include a split (not shown) to facilitate compressing distal ring 14 as distal ring 14 is inserted through incision I in patient P. Distal ring 14 is incorporated into distal end 22 of sleeve 12 by wrapping distal end 22 around distal ring 14 and securing distal ring 14 within the wrapped sleeve 12 material by various known methods such as, for example, gluing, welding etc. Sleeve 12 is formed from a relatively flexible material in order to be compressible so that a portion of sleeve 12 may be inserted through incision I in patient P.

As noted hereinabove, roller assembly 16 includes rollers 18 rotatably mounted on frame assembly 20. Frame assembly 20 has a generally polygonal shape and, in this embodiment, is formed as an octagon. Thus, roller assembly 16 includes eight rollers 18. Rollers 18 are engageable with a proximal end 24 of sleeve 12 so as to roll proximal end 24 of sleeve 12 toward distal end 22 to thereby secure surgical access port 10 about tissue.

Figure 3A:
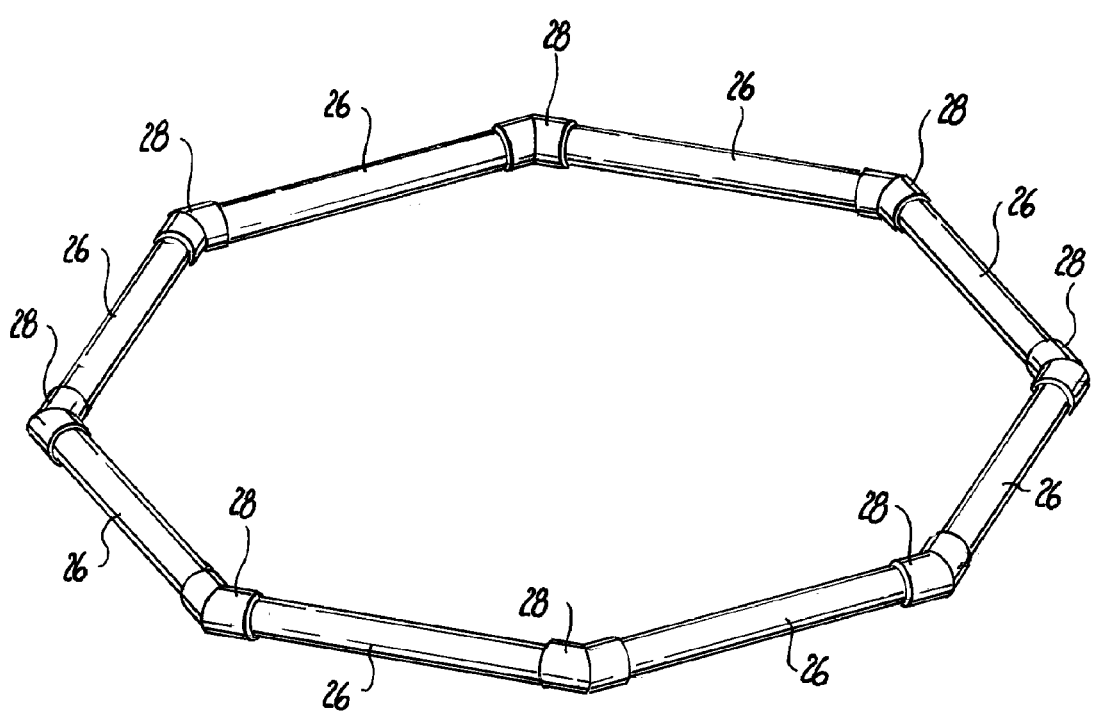
FIG. 3A is a perspective view of a frame assembly of the roller assembly.

Referring for the moment to FIG. 3A, frame assembly 20 is formed from a relatively inflexible material and may be formed as an integral unit or may be comprised of a plurality of components. Frame assembly 20 generally includes a plurality of roller supports or shafts 26 interconnected by corner members 28. Frame assembly 20 is octagonal and includes eight shafts 26. When frame assembly 20 is formed as an integral unit, it is formed by various known methods such as, for example, injection molding, stamping, etc.

Referring now to FIG. 4, shafts 26 and corner members 28 may be provided as separate components of frame assembly 20. Corner members 28 include through bores 30 for receipt of respective first and second ends 32 and 34 of shafts 26. With reference to FIGS. 4 and 5, rollers 18 are provided with roller through bores 36 for receipt of shafts 26. It should be noted that shafts 26 may be formed from a material having a relatively low coefficient of friction such as, for example, silicon coated plastics, etc. so as to facilitate the rotation of rollers 18 on shafts 26.

In order to facilitate grasping and engaging sleeve 12, rollers 18 are provided with longitudinally extending flutes 38 extending between longitudinally extending ribs 40. Ribs 40 may be further treated or textured so as to facilitate engaging sleeve 12.

Referring for the moment to FIG. 6, through bores 30 of corner members 28 have diameters d1 which are only fractionally larger than outer diameters d2 of shafts 26 so as to frictionally engage and secure an end, such as, for example first ends 32 within through bores 30 of corner members 28. First and second ends 32 and 34, respectively, may be secured within through bores 30 of corner members 28 by various known methods such as, for example, gluing, welding etc. Through bores 36 of roller members 18 have inner diameters d3 which are larger than diameters d2 of shafts 26 to allow rollers 18 to rotate about shaft members 26.

As shown, corner members 28 have outer diameters d4 which are significantly larger than inner diameters d3 of rollers 18. By providing corner members 28 with larger outer diameters d4 than the inner diameter d3 of rollers 18, rollers 18 are prevented from sliding over corner members 28 thereby preventing rollers 18 from binding or sticking on corner members 28 during rotation.

Figure 7:
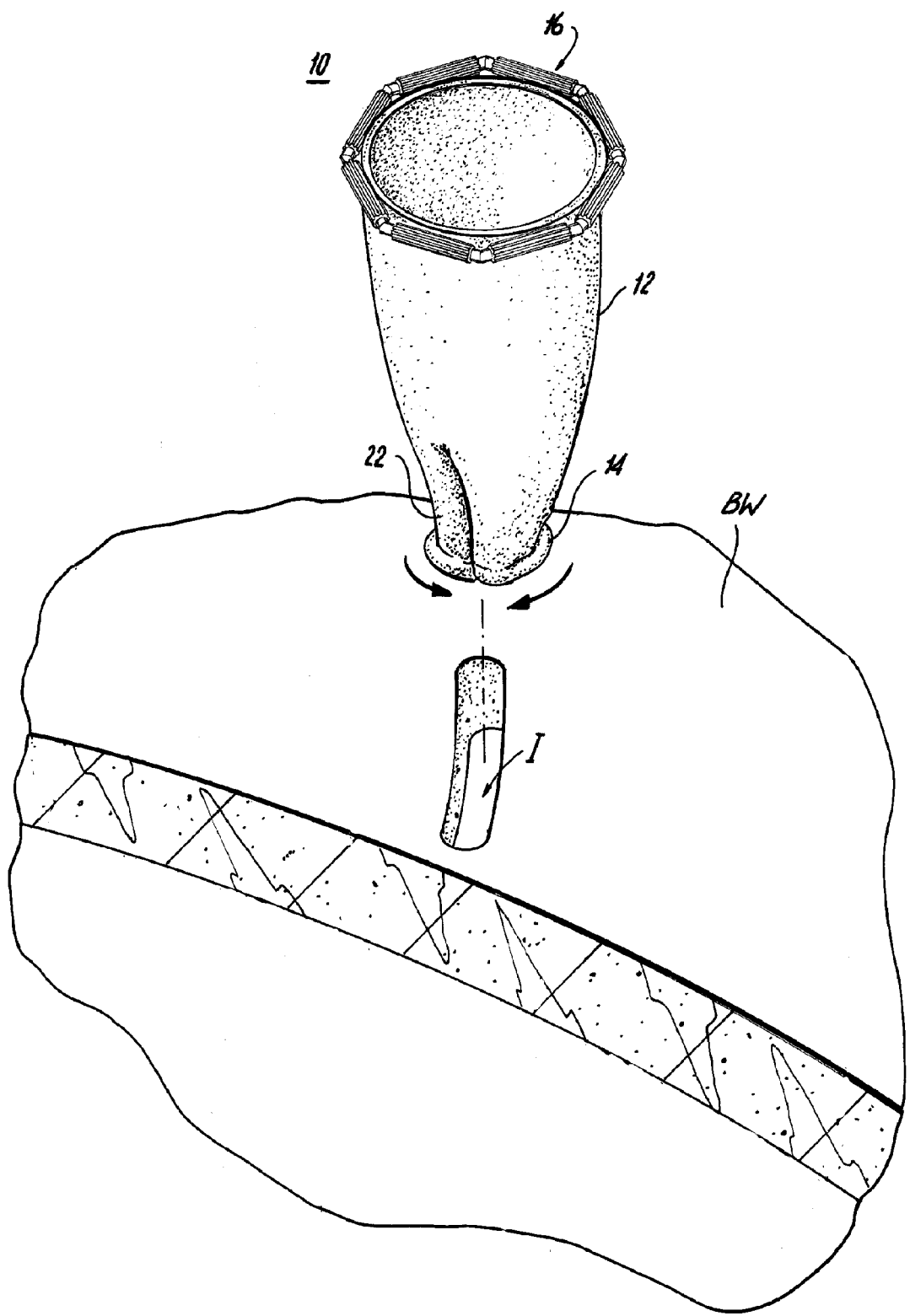
FIG. 7 is a perspective view, partially shown in section, illustrating the initial insertion of the surgical access port toward an incision formed in a body wall of a patient.

Referring now to FIGS. 7-13, and initially with regard to FIG. 7, the use of surgical access port 10 will now be described. Initially, an incision I is formed through the body wall BW of patient P (FIG. 1), for example, the abdominal wall. Surgical access port 10 is positioned adjacent incision I and distal end 22 of sleeve 12, including distal ring 14, is compressed so as to fit through incision I.

Figure 8:
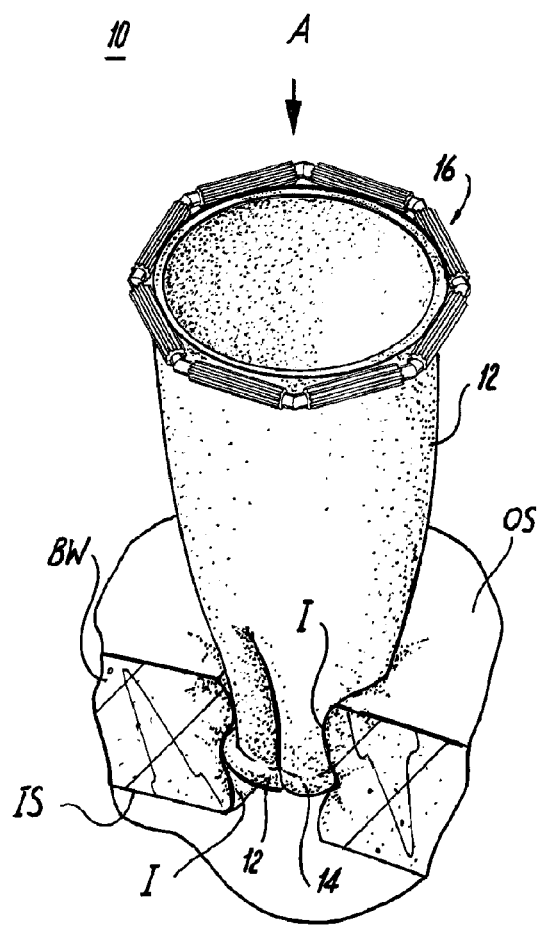
FIG. 8 is a perspective view, partially shown in section, of the surgical access port during insertion into the incision.
Figure 9:
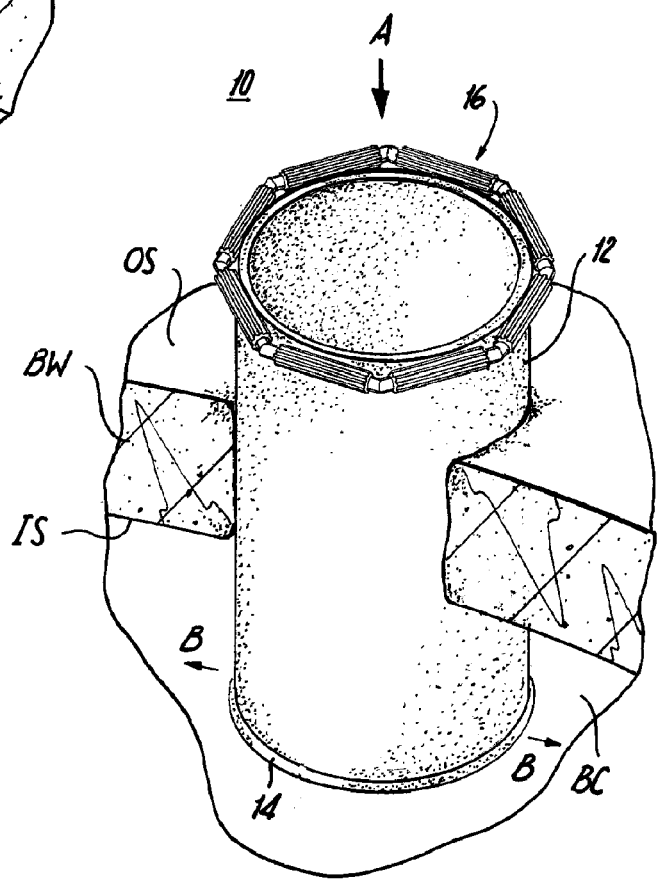
FIG. 9 is a perspective view, partially shown in section, of the surgical access port with a sleeve of the surgical access port fully inserted through the incision in the body wall of the patient.

Referring now to FIGS. 8 and 9, surgical access port 10, and specifically distal end 22 of sleeve 12 is advanced through incision I distally in the direction of arrow A. With specific reference to FIG. 9, once distal end 22 of sleeve 12, and distal ring 14, pass into a body cavity BC, distal ring 14 expands from the compressed state during insertion to a reexpanded state thereby expanding distal end 22 of sleeve 12 back to its original shape.

Figure 10:
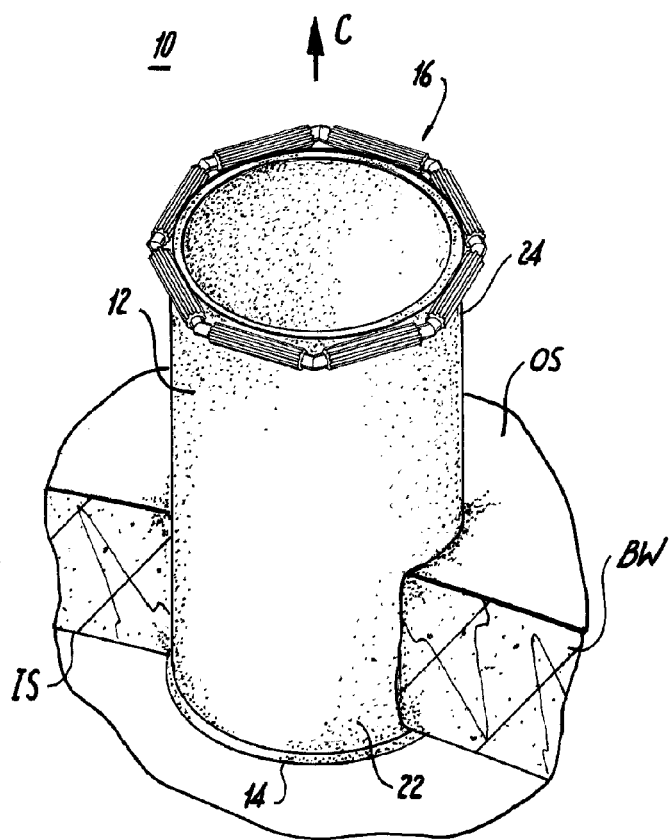
FIG. 10 is a perspective view, partially shown in section, of the surgical access port during tensioning to bring a distal ring of the surgical access port into contact with an inner surface of the body wall.

Referring to FIG. 10, thereafter, sleeve 12 is drawn proximally in the direction of arrow C so as to tension distal end 22 of sleeve 12 and distal ring 14 against an inner surface IS of body wall BW. As noted here in above, roller assembly 16 is engageable with proximal end 24 of sleeve 12 in order to facilitate rotating sleeve 12 toward an outer surface OS of body wall BW. In one method, rollers 18 are affixed proximal end 24 of sleeve 12 as discussed herein above.

Figure 11:
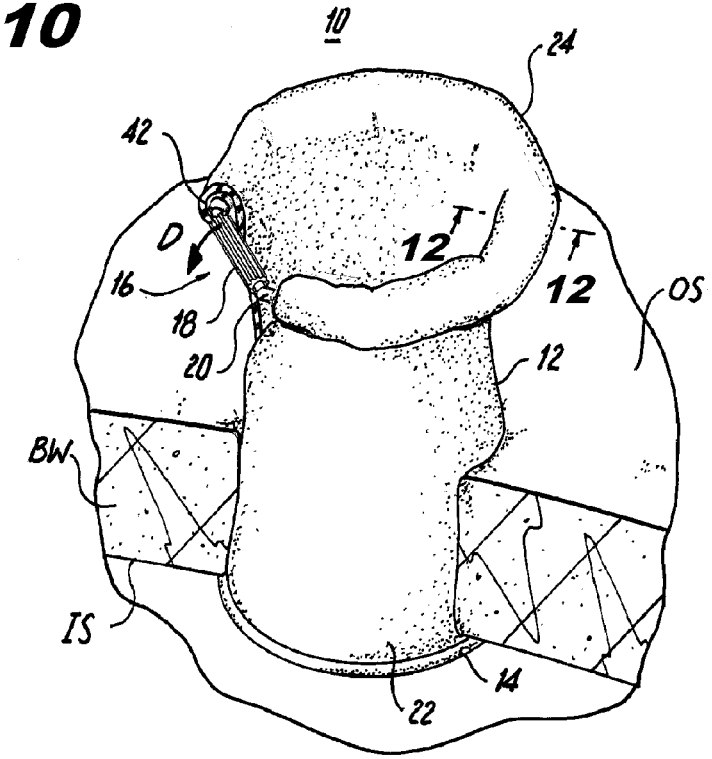
FIG. 11 is a perspective view, partially shown in section, illustrating initial rolling of a proximal end of the sleeve over the roller assembly.
Figure 12:
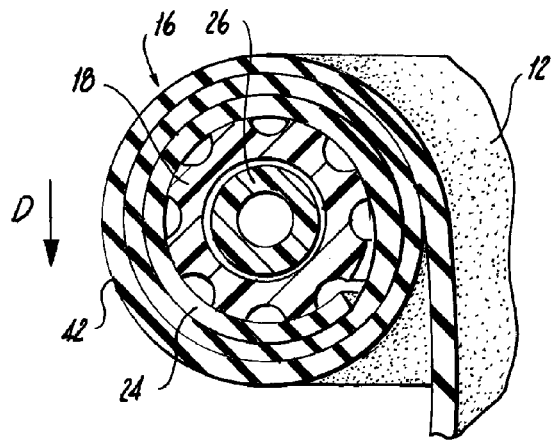
FIG. 12 is a cross-sectional view taking along line 12-12 of FIG. 11.

Referring now to FIGS. 11 and 12, in order to secure surgical access port 10 within body wall BW of patient P (FIG. 1), rollers 18 of roller assembly 16 are rotated about frame assembly 20 to begin rolling proximal end 24 of sleeve 12 counterclockwise in the direction of arrow D. as noted here in above, proximal end 24 of sleeve 12 may be affixed to one or more longitudinally extending ribs 40 of rollers 18 or, alternatively proximal end 24 of sleeve 12 may be grasped pinched against rollers 18 until proximal end 24 of sleeve 12 has made a complete rotation and secures against itself. Proximal end 24 of sleeve 12 is rotated in a counterclockwise direction so as to rotate sleeve 12 outwardly thereby preventing any obstructions to surgical instruments (not shown) inserted through surgical access port 10. As proximal end 24 of sleeve 12 is rotated, it forms a rolled sleeve portion 42 about rollers 18 and shafts 26 of roller assembly 16. The number of rolls of the material of sleeve 12 in rolled sleeve portion 42 is dependent upon the thickness of the tissue surgical access port 10 is inserted through.

Figure 13:
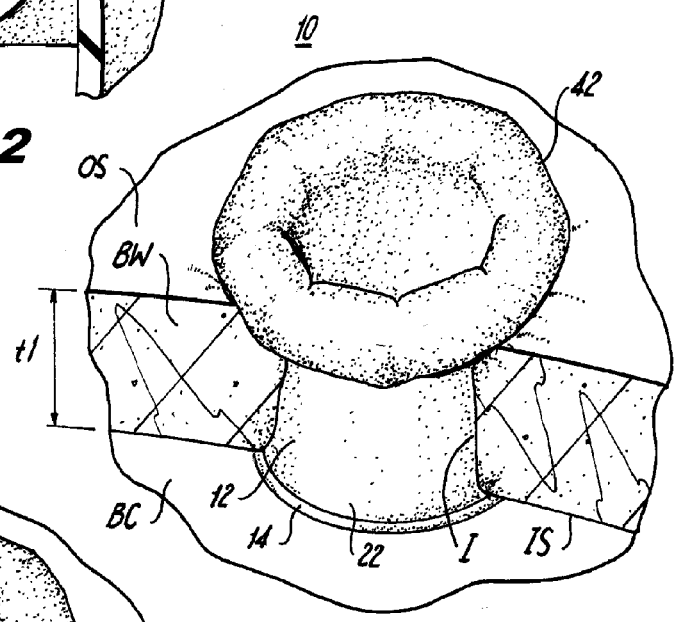
FIG. 13 is a perspective view, partially shown in section, of the surgical access port fully seated through the incision in the body wall of the patient and with the proximal end of the sleeve fully rolled down to engage in outer surface of the body wall.

Referring to FIG. 13, rolled sleeve portion 42 is rolled distally toward outer surface OS of body wall BW until rolled sleeve portion 42 engages outer surface OS thereby securing surgical access port 10 within body wall BW. It should be noted that, frame assembly 20 does not rotate but merely translates distally toward outer surface OS of body wall BW as rolled sleeve portion 42 moves distally. Rolled sleeve portion 42 of sleeve 12 is maintained in engagement with outer surface OS of body wall BW by the polygonal shape of frame assembly 20 which restricts rolled sleeve portion 42 from unraveling. In this disclosed application of surgical access port 10, body wall BW has a tissue thickness t1 and rolled sleeve portion 42 includes a first number of rolls of sleeve 12.

Figure 14:
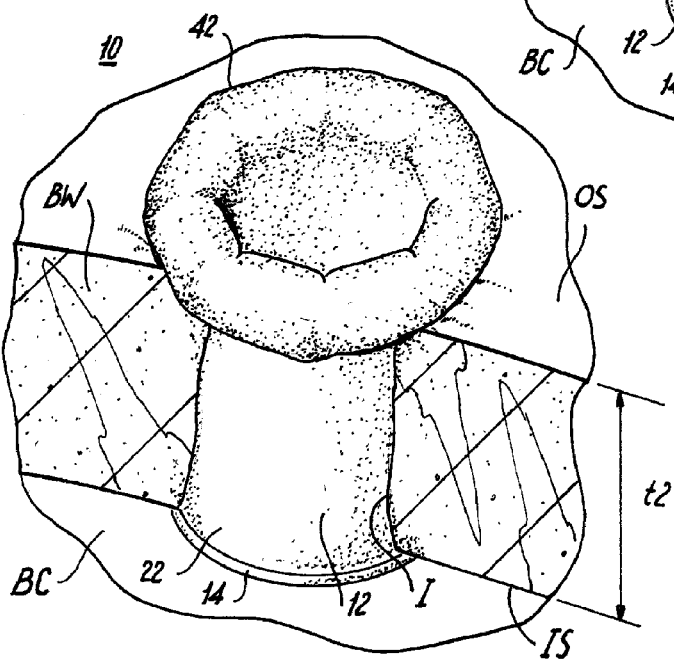
FIG. 14 is a perspective view similar to FIG. 13 with the surgical access port inserted through a body wall having a different thickness than the body wall illustrated in FIG. 13.

Referring now to FIG. 14, in a second disclosed application of surgical access port 10, surgical access port 10 is installed through body wall BW in a manner described herein above and rolled sleeve portion 42 is rolled until it engages outer surface OS of body wall BW. In this second disclosed application, body wall BW as a tissue thickness t2 which is greater than the tissue thickness t1 of body wall BW in the first disclosed application. Thus, in this second disclosed application of surgical access port 10, rolled sleeve portion 42 includes fewer rolls than the first number rolls of sleeve 12 in the first disclosed application of surgical access port 10.

Therefore, as disclosed here in above, surgical access port 10 provides an adjustable access port which can be configured depending upon the thickness of the tissue encountered. Additionally, rolled sleeve portion 42 of sleeve 12 provides a low-profile relative to outer surface OS of body wall BW thereby allowing surgical instruments to be inserted through surgical access port 10 at relatively greater angles than would be the case with more rigid surgical access ports extending above the outer surface OS of body wall BW. This allows the inserted surgical instruments to reach a greater area within body cavity BC minimizing the need for an excessive number surgical access ports.

It will be understood that various modifications may be made to the embodiments disclosed herein. For example, the roller assembly of the disclosed surgical access port may have a polygonal shape with more or less than eight sides or may take a rectangular or even triangular shape. Further, the disclosed surgical access port may be provided as a fully assembled structure with the rollers of the roller assembly firmly affixed to the proximal end of the sleeve. Further, the disclosed rollers may have other surface profiles such as, for example, smooth, textured, etc. to facilitate engaging the proximal end of the sleeve. Additionally, the disclosed rollers may have cross-sectional shapes other than circular such as, for example, rectangular, triangular, etc. to facilitate securing the rolled portion of the sleeve against an outer surface of the body tissue. Although the access port of the present disclosure has been described to access an abdominal cavity through an incision in the abdominal wall, the access port of the present disclosure may be modified for use in other procedures, such as, for example, thoracic procedure. Therefore, the above description should not be construed as limiting, but merely as exemplifications of particular embodiments. Those skilled in the art will envision other modifications within the scope and spirit of the claims appended hereto.

The invention claimed is:

1. A surgical access port comprising:
a flexible sleeve having proximal and distal ends; and
a roller assembly engageable with the proximal end of the flexible sleeve, the roller assembly including a frame assembly having a polygonal shape, the frame assembly including a plurality of shafts and a plurality of rollers rotatably supported on the plurality of shafts, the plurality of shafts interconnected by a plurality of corner members, each roller of the plurality of rollers defining a through bore configured to receive a respective shaft of the plurality of shafts, each corner member of the plurality of corner members having an outer diameter larger than an inner diameter of the through bore of each roller of the plurality of rollers to inhibit binding of a respective roller of the plurality of rollers on a respective corner member of the plurality of corner members.

2. The surgical access port as recited in claim 1, wherein the frame assembly has an octagonal shape.

3. The surgical access port as recited in claim 1, wherein the frame assembly is formed as an integral member.

4. The surgical access port as recited in claim 1, wherein the frame assembly is formed from a plurality of components including individual shafts and corner members.

5. The surgical access port as recited in claim 1, wherein each roller of the plurality of rollers includes longitudinally extending ribs separated by longitudinally extending flutes.

6. The surgical access port as recited in claim 5, wherein at least one of the longitudinally extending ribs of at least one roller of the plurality of rollers is secured to the proximal end of the flexible sleeve.

7. The surgical access port as recited in claim 5, wherein at least one of the longitudinally extending ribs of the respective roller is secured to the proximal end of the flexible sleeve.

8. The surgical access port as recited in claim 5, wherein the longitudinally extending ribs are textured so as to facilitate engagement with the proximal end of the flexible sleeve.

9. The surgical access port as recited in claim 1, wherein the plurality of shafts are formed of a material configured to facilitate rotation of the plurality of rollers on the plurality of shafts.

10. The surgical access port as recited in claim 1, further comprising a flexible ring provided on the distal end of the flexible sleeve.

11. A surgical access port comprising:
a flexible sleeve having proximal and distal ends; and
a roller assembly provided at the proximal end of the flexible sleeve, the roller assembly including a polygonal frame assembly having a plurality of shafts interconnected by a plurality of corner members and a plurality of rollers rotatably mounted on the plurality of shafts, the plurality of rollers being engageable with the proximal end of the flexible sleeve, each corner member of the plurality of corner members having an outer diameter larger than an inner diameter of a through bore defined in each roller of the plurality of rollers to prevent binding of each roller of the plurality of rollers on a respective corner member of the plurality of corner members; and
a flexible ring affixed to the distal end of the flexible sleeve.

12. The surgical access port as recited in claim 11, wherein the polygonal frame assembly forms an octagon.

13. The surgical access port as recited in claim 11, wherein the plurality of rollers are affixed to the proximal end of the flexible sleeve.

14. A method of providing a surgical access port in the body of a patient:
providing a surgical access port including:
a flexible sleeve having proximal and distal ends;
a roller assembly engageable with the proximal end of the sleeve, the roller assembly including a frame assembly having a polygonal shape and a plurality of rollers rotatably mounted on the frame assembly, the frame assembly including a plurality of shafts rotatably supporting the plurality of rollers, the plurality of shafts interconnected by a plurality of corner members, each roller of the plurality of rollers defining a through bore configured to receive a respective shaft of the plurality of shafts, each corner member of the plurality of corner members having an outer diameter larger than an inner diameter of the through bore of a respective roller of the plurality of rollers to inhibit binding of each roller of the plurality of rollers on a respective corner member of the plurality of corner members, the roller assembly engageable with the proximal end of the flexible sleeve; and
a flexible ring provided on the distal end of the flexible sleeve;
inserting the distal end of the flexible sleeve through an incision formed in a body wall of a patient by compressing the flexible ring and inserting the flexible ring distally through the incision until it passes into a body cavity;
tensioning the surgical access port in a proximal direction to bring the flexible ring into engagement with an inner surface of the body wall;
engaging the plurality of rollers with the proximal end of the flexible sleeve and rotating the plurality of rollers to roll the flexible sleeve about the frame assembly and form a rolled portion of the flexible sleeve; and
rolling the rolled portion of the flexible sleeve until it engages an outer surface of the body wall.

15. The method as recited in claim 14, wherein engaging the plurality of rollers with the proximal end of the flexible sleeve and rotating the plurality of rollers includes rotating the plurality of rollers affixed to the proximal end of the flexible sleeve.

* * * * *